United States Patent
Ghammraoui et al.

(10) Patent No.: US 9,599,580 B2
(45) Date of Patent: Mar. 21, 2017

(54) DIFFRACTOMETRY-BASED ANALYSIS METHOD AND ASSOCIATED DIFFRACTOMETER, PARTICULARLY SUITABLE FOR SAMPLES COMPRISING MULTIPLE LAYERS OF MATERIALS

(71) Applicant: Commissariat a l'Energie Atomique et Aux Energies Alternatives, Paris (FR)

(72) Inventors: Bahaa Ghammraoui, Nord du Liban (LB); Caroline Paulus, Saint-Martin d'Heres (FR); Joachim Tabary, Grenoble (FR)

(73) Assignees: COMMISSARIAT A L'ENERGIE ATOMIQUE ET AUX ENERGIES ALTERNATIVES, Paris (FR); MOZIDO, INC., Austin, TX (US)

( * ) Notice: Subject to any disclaimer, the term of this patent is extended or adjusted under 35 U.S.C. 154(b) by 117 days.

(21) Appl. No.: 14/428,721

(22) PCT Filed: Sep. 19, 2013

(86) PCT No.: PCT/FR2013/052173
§ 371 (c)(1),
(2) Date: Mar. 31, 2015

(87) PCT Pub. No.: WO2014/044982
PCT Pub. Date: Mar. 27, 2014

(65) Prior Publication Data
US 2016/0033427 A1 Feb. 4, 2016

(30) Foreign Application Priority Data

Sep. 20, 2012 (FR) .................... 12 58851

(51) Int. Cl.
*G01T 1/36* (2006.01)
*G01N 23/20* (2006.01)

(52) U.S. Cl.
CPC . *G01N 23/20091* (2013.01); *G01N 2223/639* (2013.01)

(58) Field of Classification Search
CPC ....... G01N 2223/639; G01N 23/20091; A61K 45/06; A61K 31/5377; A61K 31/277;
(Continued)

(56) References Cited

U.S. PATENT DOCUMENTS 5,007,072 A 4/1991 Jenkins
7,474,732 B2 * 1/2009 Berman ............... G01N 23/201
378/205

(Continued)

FOREIGN PATENT DOCUMENTS

FR 2956216 A1 8/2011

OTHER PUBLICATIONS

Ordavo, I., et al. "A new pnCCD-based color X-ray camera for fast spatial and energy-resolved measurements", Nuclear Instruments & Methods in Physics Research. Section A: Accelerators, Spectrometers, Detectors, and Associated Equipment, Elsevier BV, North Holland, Netherlands vol. 654, No. 1, May 29, 2011, pp. 250-257.
(Continued)

*Primary Examiner* — Irakli Kiknadze
(74) *Attorney, Agent, or Firm* — Brinks Gilson & Lione (57) ABSTRACT

A method and device that analyzes a sample with a diffractometer that includes a collimated source, a spectrometric detector, and a detection collimator. The sample is irradiated with an incident beam and the detector has a detection plane with multiple physical or virtual pixels. An measured energy spectrum is established for each pixel and each measured energy spectrum is readjusted. The spectrum is expressed as (Continued)

a function of a variable that accounts for the energy of the scattered radiation and an angle of diffraction. The fulfillment of at least one multiple material criterion is verified. Groups of pixels are formed using the results of the verification step, each group corresponding to a layer of material and different groups corresponding to different layers of material, and the spectra are combined by group, during which, for each group, the readjusted spectra for the pixels of the group are combined.

15 Claims, 5 Drawing Sheets

(58) Field of Classification Search
CPC .. A61K 31/337; A61K 31/497; A61K 31/715; A61K 31/444; A61K 31/4545; A61K 31/4745; A61K 31/502; A61K 31/5025; A61K 31/551; A61K 31/58; A61K 31/495; C07D 239/42; C07D 401/12; H01L 2924/0002; H01L 2924/00; H01L 22/12; H01L 2251/558; H01L 27/3244; H01L 27/3281; H01L 51/0051; H01L 51/0061; H01L 51/0071; H01L 51/0077; H01L 51/50; H01L 51/5088; H01L 51/5092; H01L 51/5262; H01L 51/4226
USPC .................................... 378/70, 71, 83, 86
See application file for complete search history.

(56) References Cited

U.S. PATENT DOCUMENTS

| | | | |
|---|---|---|---|
| 7,595,489 B2* | 9/2009 | Statham | G01N 23/22 250/307 |
| 2006/0140340 A1 | 6/2006 | Kravis | |
| 2011/0164730 A1* | 7/2011 | Yokhin | G01N 23/207 378/73 |

OTHER PUBLICATIONS

Harding, G. et al. "X-Ray Diffraction Imaging—A Multi-Generational Perspective", Applied Radiation and Isotopes, Elsevier, Oxford, GB, vol. 67, No. 2, pp. 287-295.
International Search Report of PCT/FR2013/052173 issued May 8, 2014, 8 pages.

* cited by examiner

DIFFRACTOMETRY-BASED ANALYSIS METHOD AND ASSOCIATED DIFFRACTOMETER, PARTICULARLY SUITABLE FOR SAMPLES COMPRISING MULTIPLE LAYERS OF MATERIALS

TECHNICAL FIELD

The present invention concerns a method of analyzing a material by diffractometry, and an associated diffractometer.

BACKGROUND

It is known to use diffractometry to detect certain crystalline substances such as most explosives or numerous other dangerous or illegal structures. Within a crystal, which is an arrangement of atoms, elastically scattered electromagnetic waves interfere with each other to give scattering which is coherent at the scale of the crystal. When those interferences are constructive, they may be detected by the measurement of a diffracted ray and by the identification of the diffraction peaks. Thus, the constructive interferences are located by an appearance of diffraction peaks (or Bragg peaks) in the radiation diffused by a material.

To know whether a given crystalline substance is contained in a material, it is thus known to:
- irradiate a sample of the material using an incident beam with a central axis X, emitted by a source,
- study the diffracted radiation using a detection device comprising
  - a detector, here termed spectrometric detector, configured to establish an energy spectrum of the radiation diffused at a given scatter angle, that is to say a detector comprising
- a detector material, which, on the near side to the sample of materials, presents a plane here termed detection plane,
- means, here termed spectrometry measurement means, configured to measure an energy released by each interaction of a photon with the detector material and to establish at least one energy spectrum, denoted S(E).
- a collimator, here termed detection collimator, associated with the detector, the detector and the detection collimator being arranged so as to have a detection axis D, the detection axis D forming a diffraction angle θ with the central axis X of the incident beam.

It is to be noted that an energy spectrum illustrates the energy distribution of radiation in the form of a histogram representing the number of photon interactions in the material (along the y-axis) according to the released energy (along the x-axis). Generally, the energy axis is discretized into channels of width 2 $\delta E$, a channel $C_i$ corresponding to the energies comprised between $E_i - \delta E$ and $E_i + \delta E$.

The various peaks obtained on an energy spectrum of a radiation that is scattered, at an angle θ, are characteristic of the material analyzed, since the scattered radiation participating in the constructive interferences satisfies the following equation:

$$E_{hkl} = n \frac{hc}{2d_{hkl}\sin(\theta/2)}$$

with:
$d_{hkl}$: interplanar spacing between the crystallographic planes of the irradiated crystal;

θ: scatter angle, that is to say the angle formed between the scattered ray analyzed and the beam that is incident on the irradiated crystal
h: Planck's constant
c: the speed of light
n: the order of the interference:

This property is exploited in well-known methods, designated by the acronym EDXRD or "Energy Dispersive X-Ray Diffraction".

WO2008/142446 describes a method of determining the composition of an object by the spectrometric detection of an object irradiated by x-ray radiation. In the description of the prior art of WO2008/142446, reference is made to baggage checking. The method described comprises the following steps:
- irradiating the object, particularly for example using x-ray radiation,
- detecting the intensity transmitted through the object using a spectrometric detector. It is to be noted that the radiation studied here is the radiation transmitted by the sample of materials and is not diffracted; in other words, the detection axis D coincides with the axis X of the incident beam,
- selecting energy bands in the transmitted spectrum, and establishing transmission quantities in each of those bands,
  comparing at least two of said obtained quantities.

According to a first embodiment, it is sought to identify the material by detecting a Bragg detection signature. For this, a discontinuity in the transmitted intensity is revealed, at a given energy, or at least within a narrow energy band. This discontinuity is assumed to correspond to a localized drop in the amplitude of the transmitted signal under the effect of elastic scattering (Bragg diffraction) in the crystal lattice of the material analyzed. This scattering only occurs for certain discrete incident energies Ei and it is considered that in the neighborhood of that energy, the transmitted signal decreases. Thus, by comparing the intensity of the signal transmitted at that energy in a narrow energy band centered on Ei with the signal transmitted at another energy, the presence of a particular material is detected. In other words, in this application, analysis is made of the radiation transmitted by the object, and in particular of the discontinuities in its energy spectrum on account of Bragg diffraction.

In diffractometry, two parameters are essential to obtain a reliable and effective detection system: sensitivity and energy resolution. As always, these two parameters vary inversely: the improvement of one is accompanied by the degradation of the other. In a previous application FR11/62497 the inventors provided a method and device for analyzing a sample of materials by diffractometry, of which the energy resolution is improved, in order to obtain clearer separation of the diffraction peaks for a better identification of materials. In that earlier method:
- a diffractometer is used which comprises
  - a source configured to emit an incident beam with a central axis X,
  - a detector comprising
    - a detector material, which, on the near side to the sample of materials, presents a plane here termed detection plane,
    - means, here termed spectrometry measurement means, configured to measure an energy released by each photon interaction with the detector material and to establish at least one energy spectrum, denoted S(E), the detector being here termed spectrometric detector on account of this;

means for locating an interaction of a photon with the detector material, making it possible to define a partition of the detector in physical or virtual pixels, and making it possible to associate one of said pixels with each photon interaction; the detector used being here termed a pixelated detector on account of this;

a collimator, here termed detection collimator, associated with the detector, the detector and the detection collimator being arranged so as to have a detection axis D forming a diffraction angle θ with the central axis X of the incident beam, the sample is irradiated with the incident beam, an energy spectrum Si(E) is established for each pixel of the detector, the energy spectra obtained earlier are combined.

The gain in energy resolution obtained by virtue of the method and the device of FR11/62497 makes increasing the sensitivity possible, while keeping a very satisfactory energy resolution. To improve the sensitivity, it suffices to increase the opening of the detection collimator in order to collect more signal. But the observed field (or inspection volume, defined as being the volume, in the sample of materials, delimited by the incident beam and further delimited by the solid angle by which the detector sees the sample of materials—that is to say the solid angle delimited by the opening of the detection collimator and the detection plane of the detector —) is then greater, with an increased risk of superposition of materials, which may complicate the interpretation of the spectra obtained.

SUMMARY

The invention is directed to solving this problem by providing a method and a device which are particularly configured for the analysis of samples comprising several layers of materials. In this way, it becomes possible to use an open detection collimator to obtain a device which is both sensitive, by virtue of that opening, and which has a good energy resolution thanks to its pixelated detector.

Another objective of the invention is to attain that aim without significant increase in the manufacturing costs of the device nor of its bulk.

To that end, the invention provides a method of analyzing a sample of materials, wherein:

a diffractometer is used which comprises a source configured to emit an incident beam with a central axis X, a spectrometric pixelated detector as defined previously, a detection collimator, associated with the detector, the detector and the detection collimator being arranged so as to have a detection axis D forming a diffraction angle θ with the central axis X of the incident beam, the sample is irradiated with the incident beam, an energy spectrum Si(E), here termed measured spectrum, is established for each pixel of the detector, adjustment of each measured energy spectrum is made, by expressing said energy spectrum according to a variable taking into account the energy of the scattered radiation and the diffraction angle $\theta_i$, a spectrum referred to as adjusted spectrum is thus obtained for each measured spectrum, the fulfillment of at least one criterion, here termed multimaterial criterion, representing the presence of several layers of material, is verified, groups of pixels are formed using results of the preceding verifying step, each group corresponding to a layer of material, different groups corresponding to different layers of material, a step of combining spectra by group is carried out, wherein, for each group, the adjusted spectra obtained for the pixels of said group are combined.

Advantageously and in accordance with the invention, the adjusted spectra established are spectra $S_i(x)$ in terms of momentum transfer, the change in variable being carried out using the following formula:

$$x = \frac{\sin(\theta_i/2)}{\lambda} = \frac{E\sin(\theta_i/2)}{hc},$$

where $\theta_i$ designates the diffraction angle corresponding to the pixel Pi that is to say the angle between the axis X of the incident beam and the axis Di passing by the center of the pixel Pi and the center of the detection collimator, and λ is the wavelength corresponding to the energy E.

The variable change made in the step of adjusting the spectra then makes it possible, in the step of combining spectra, to directly combine arithmetically (for example to sum, when the variable used is the momentum transfer) adjusted spectra corresponding to different pixels. It thus provides a method of combining spectra which is extremely simple, which may be implemented using computing means with low energy and memory requirements.

In all that follows:

"diffraction plane" is used to mean a plane (X,D) defined by the axis X of the incident beam and the detection axis D, "transverse direction" is used to mean a direction orthogonal to the axis D and contained in the diffraction plane, "lateral position of a pixel Pi of the detector" is used to mean a coordinate of the pixel Pi in the transverse direction, "position in a spectrum of an energy peak or of a local maximum" is used to mean the channel or the energy or the momentum transfer x (this is a case of an adjusted spectrum) corresponding to said peak.

Advantageously and according to the invention, each multimaterial criterion is chosen from among:

a significant variation, for example greater than 10%, of the position of a first local maximum, defined as being the first peak detected along the x-axis in the adjusted spectra, between two adjacent pixels in the transverse direction; in what follows, this criterion is called multimaterial criterion of the first local maximum, a significant variation, for example greater than 10%, of the position of a second local maximum, defined as being the second peak detected along the x-axis in the adjusted spectra, between two adjacent pixels in the transverse direction; in what follows, this criterion is called multimaterial criterion of the second local maximum, a significant variation, for example greater than 10%, of the sum of the channels of the adjusted spectrum (in other words of the integral of the adjusted spectrum, that is to say of the area delimited by the curve of the adjusted spectrum and the x-axis) for each pixel, between two adjacent pixels in the transverse direction.

Preferably, to verify the fulfillment of the multimaterial criterion of the first (respectively second) local maximum defined above, a curve is constructed wherein the y-axis represents the position in the spectrum of the first (respectively the second) local maximum and wherein the x-axis represents the lateral position Yi of the pixel Pi or its diffraction angle θi. This curve presents at least one "jump", that is to say an increase or a reduction of more than 10% along the y-axis between two adjacent pixels, and thus over a variation in terms of x-coordinates less than a maximum dimension of the pixels in the transverse direction.

Each value Yi of the lateral position in which such a jump is involved is used for forming groups of pixels. All the pixels of which the position lateral Yi (or diffraction angle θi) is comprised between two consecutive jumps are considered as belonging to the same group.

Preferably, the method of analysis according to the invention comprises verifying the fulfillment of two multimaterial criteria.

The invention also relates to a diffractometer configured to implement the method according to the invention. In particular, the invention provides a diffractometer comprising:
- a source configured to emit an incident beam with a central axis X,
- a spectrometric pixelated detector as defined earlier,
- a detection collimator, associated with the detector, the detector and the detection collimator being arranged so as to have a detection axis D forming a diffraction angle θ with the central axis X of the incident beam.

The diffractometer according to the invention is characterized in that:
the detector is pixelated in that it comprises means for locating an interaction of a photon with the detector material (30), making it possible to define a partition of the detector in physical or virtual pixels, and making it possible to associate one of said pixels with each photon interaction;
the spectrometry measuring means are configured to establish an energy spectrum $S_i(E)$ for each pixel of the detector,
the diffractometer further comprises:
computing means, referred to as adjusting means, configured to establish, for each measured energy spectrum, a spectrum referred to as adjusted spectrum expressed according to a variable taking into account the energy of the scattered radiation and the diffraction angle θi,
means for verifying the fulfillment of at least one criterion, here termed multimaterial criterion, representing the presence of several layers of materials,
means for forming groups of pixels, each group corresponding to a layer of material, different groups corresponding to different layers of material,
means for combining spectra by group, adapted, for each group, to selectively combine only the adjusted spectra obtained for the pixels of said group.

Preferably, the adjusting means are configured to establish, for each energy spectrum measured, a momentum transfer spectrum $S_i(x)$, by change in variable using the formula indicated above. The combining means are thus configured to sum adjusted spectra.

Advantageously and according to the invention, the means for verifying at least one multimaterial criterion are configured to verify the multimaterial criterion of the first local maximum. In this case, they are preferably configured to establish a curve wherein the y-axis represents the position in the spectrum of a first local maximum and wherein the x-axis represents an angle of diffraction θi of the pixel Pi or a lateral position Yi of the pixel Pi defined as being a coordinate of the pixel Pi in a transverse direction (T), orthogonal to the detection axis D and contained in a detection plane (X,D). The means for forming groups of pixels are thus configured to group together within the same group two adjacent pixels Pi and $P_{i+1}$ in the transverse direction if and only if the difference between the position of the first local maximum in the adjusted spectrum of the pixel Pi and the position of the first local maximum in the adjusted spectrum of the pixel $P_{i+1}$ do not vary by more than 10%.

Advantageously and according to the invention, the means for verifying at least one multimaterial criterion are, as a variant or in addition, configured to verify the multimaterial criterion of the second local maximum. In this case, they are preferably configured to establish a curve representing, along the y-axis, the position in the adjusted spectrum (of the pixel Pi) of a second local maximum, based, along the x-axis, on the angle of diffraction θi of the pixel Pi or on the lateral position Yi thereof. The means for forming groups of pixels are thus configured to group together within the same group two adjacent pixels Pi and $P_{i+1}$ in the transverse direction if and only if the difference between the position of the second local maximum in the adjusted spectrum of the pixel Pi and the position of the second local maximum in the adjusted spectrum of the pixel $P_{i+1}$ do not vary by more than 10%.

Advantageously, the method and the diffractometer according to the invention have one or more of the following features, all the possible combinations being in accordance with the invention:
the detector is of the type with a detector material of semiconductor, which does not exclude the possibility of using a detector of the scintillator-based detector type. Semiconductor-based detectors are generally preferred for their better energy resolution and for their smaller bulk,
the source is a polychromatic source;
the source delivers radiation having a maximum energy comprised between 10 and 1000 keV, preferably between 10 and 200 keV; the diffractometer comprises a collimator, here termed source collimator, associated with the radiation source;
the source collimator delimits the irradiating beam according to an axis Y of the diffraction plane which is orthogonal to the axis X of the incident beam as well as according to an axis Z which is orthogonal to the diffraction plane;
the source collimator is a collimator with a single rectangular slot; the source collimator has a thickness (dimension along the axis X of the incident beam) of 100 mm and slot height (dimension along the axis Y) of 0.10 mm;
the diffraction angle θ is low; it is preferably comprised between 2 and 10°. The observation of the diffraction phenomenon is clearest at a small angle, since coherent scatter predominates for a small momentum transfer (the momentum transfer being proportional to $\sin(\theta/2)$),
the detection collimator used is a collimator with a single rectangular (or even square) slot;
the detection collimator is a detector qualified as an open collimator: it delimits the detected beam widely in the transverse direction; for this, it has a slot of height greater than 1 mm, preferably greater than 2 mm, for example of the order of 2.5 mm. The great height of the detection collimator slot in the diffraction plane (X,D) gives high sensitivity to the analysis device but tends to degrade is angular and energy resolutions; this defect is compensated for, by virtue of the invention, through the use of a pixelated detector and by the combination by group of the different spectra obtained,
the detection collimator has a slot of length greater than 2 mm. The opening of the detection collimator along the axis Z (slot length of the detection collimator) is advantageous for increasing the signal without losing angular resolution, since the diffraction angle varies little along the axis Z according to the material, the detection collimator has a thickness (dimension along the detection axis D) of 100 mm.

BRIEF DESCRIPTION OF THE DRAWING

Other details and advantages of the present invention will appear from the reading of the following description, which refers to the diagrammatic appended drawings and which relates to preferred embodiments, provided by way of non-limiting examples. In the drawings:

FIG. 4 represents a simulation of bi-parameter spectra in lateral position which would be obtained for a sample of aluminum by a diffractometer with a pixelated detector according to the invention with an open detection collimator.

FIG. 7 represents a simulation of bi-parameter spectra in lateral position which would be obtained for the salt/graphite sample of FIG. 6 by a diffractometer with a pixelated detector according to the invention with an open detection collimator.

DETAILED DESCRIPTION

Figure 1:
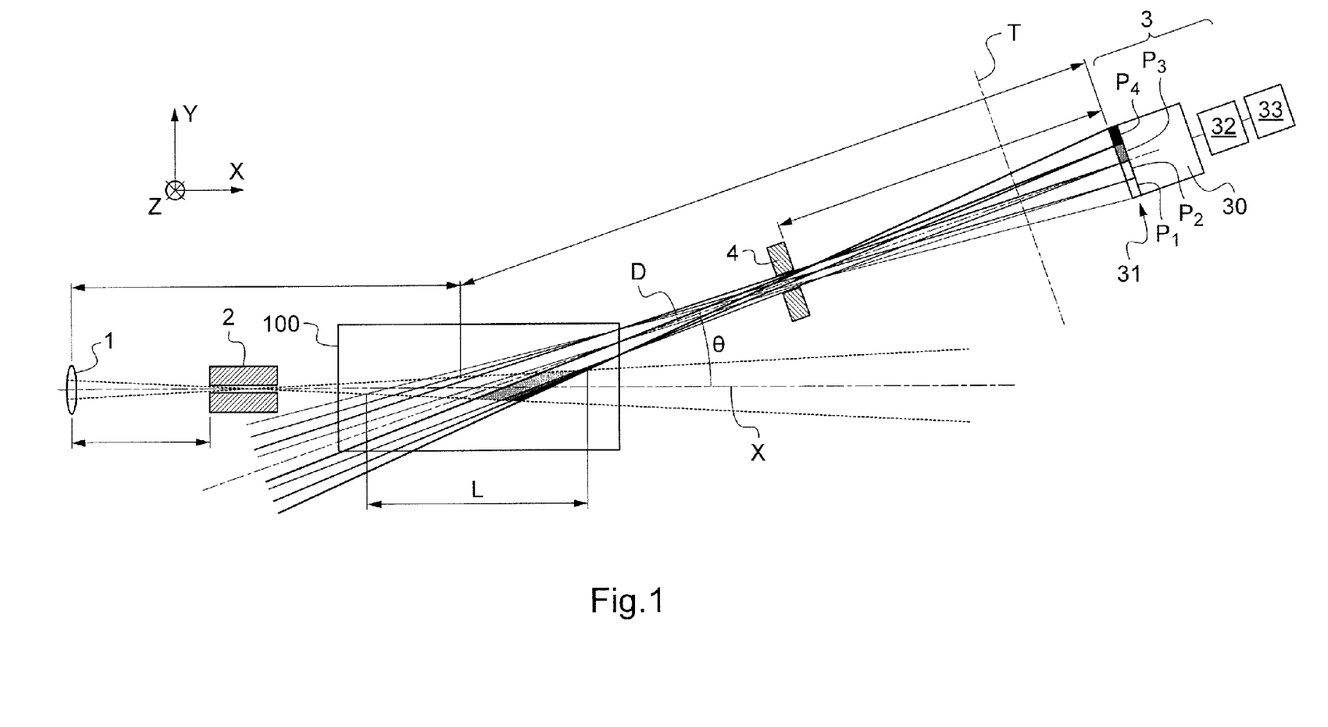
FIG. 1 is a diagrammatic view in cross-section in a diffraction plane of a diffractometer according to the invention.

FIG. 1 illustrates a diffractometer according to the invention. This comprises first of all a polychromatic source 1 of energy comprised between a few tens of keV and a few hundred keV, for example between 10 keV and 200 keV. This source 1 emits radiation that is collimated using a source collimator 2, it being possible for the latter to be produced from tungsten or tungsten alloy. As non-limiting illustrated example, this source collimator 2 has a single rectangular slot and a thickness of 100 mm and a slot height less than 0.5 mm; for example equal to 0.1 mm. It is disposed at a distance from the source 1 equal to 140 mm. The polychromatic source 1 and the source collimator 2 generate an incident beam with an axis X. The diffractometer according to the invention next has an accommodation for receiving a sample of materials 100, that accommodation being formed such that the sample of materials is irradiated by the incident beam generated by the source 1 and the source collimator 2. The diffractometer according to the invention further comprises a detector collimator 4 and a detector 3, which are aligned along a detection axis D forming with the axis X of the incident beam an angle $\theta$ here equal to 4° (the appended FIGs. are not to scale).

This detector 3 comprises a detector material 30, which, facing the detector collimator 4, presents a detection plane 31, and further comprises electronic and computer processing means 32 and 33. Preferably, the detector material 30 used here is a semiconductor material such as a material based on CdTe, CdZnTe (CZT), silicon (Si) or $HgI_2$, capable of being polarized by a cathode and an anode, that are disposed on two opposite faces of the semiconductor material. It is also possible to employ a Germanium-based detector, despite the constraints described earlier. When a photon penetrates the semiconductor material 30 and interacts with it, all or some of its energy is transferred to charge carriers (electron/hole pairs) in the semiconductor material. Because the detector is polarized, the charge carriers migrate towards the electrodes (including the anode). They then produce an electrical signal at the terminals of the electrodes. This electrical signal, the amplitude of which is proportional to the energy deposited by the photon at the time of the interaction, is collected then processed by computer means 32 and 33. The signal is preferably collected solely at the anode; it may as a variant be collected solely at the cathode, or at both electrodes. A detector with a semiconductor material usually comprises a plurality of physical pixels, each physical pixel corresponding to a circuit for charge collection by an electrode. In the known diffractometers, the detectors used have a detection plane receiving the diffracted beam which corresponds to a single pixel, referred to as full pixel Pc.

According a first major feature of the invention, the detector 3 is a pixelated detector, which means that the detection plane 31 of the semiconductor material 30 comprises several pixels Pi.

In the illustrated example, the detection plane 31 comprises a column of pixels Pi which succeed each other in the transverse direction T (orthogonal to the detection axis D). Four pixels P1 to P4 are represented here (in the interest of clarity, a small number of pixels is represented, but it is of course possible for there to be more). Each of these four pixels observes a volume of material of length (along the axis X) equal to 17.5 mm and detects the radiation diffracted at an average angle θi which can be seen more easily in FIG. 2, that is to say the radiation diffracted between the angles θi−δθ/2, and θi+δθ/2 with δθ being of the order of 0.2°. A full pixel Pc corresponding to the four pixels P1 to P4 of the detector of the diffractometer according to the invention would detect the radiation diffracted around 4° over a range of diffraction angles three times wider than that attributed to each pixel Pi.

It follows that the angular resolution of the detector of the diffractometer with a pixelated detector according to the invention is much better than that of a known diffractometer for which the detector is provided with the full pixel Pc. This directly results in an improvement in energy resolution of the detector.

The pixelation of the detection plane 31 is obtained physically using smaller pixels. The reduction in the size of the pixels however poses various problems. In particular, the manufacturing costs are considerably increased; the increased number of electronic processing channels also adversely affects the manufacturing costs and leads to production of a bulky device. The pixelation of the detection plane 31 is preferably obtained virtually using an item of location information for location, within each physical pixel, of a photon interaction taking place in alignment with that pixel. As taught by the publication "*An approach to sub-pixel spatial resolution in room temperature X-ray detector arrays with good energy resolution*" (W. K. Warburton), it is possible to determine the coordinates (x, y) of the barycenter of the charge cloud produced by an interaction, based on electrical signals generated simultaneously by that interaction on a plurality of adjacent anodes. It is thus considered that the interaction has been detected solely by the virtual pixel corresponding to the coordinates of the barycenter. In such a method, only the coordinates of the physical pixel that collected the maximum signal are used. This approach, known per se, makes it possible to divide each physical pixel into a plurality of virtual pixels in the detection plane.

Figure 2:
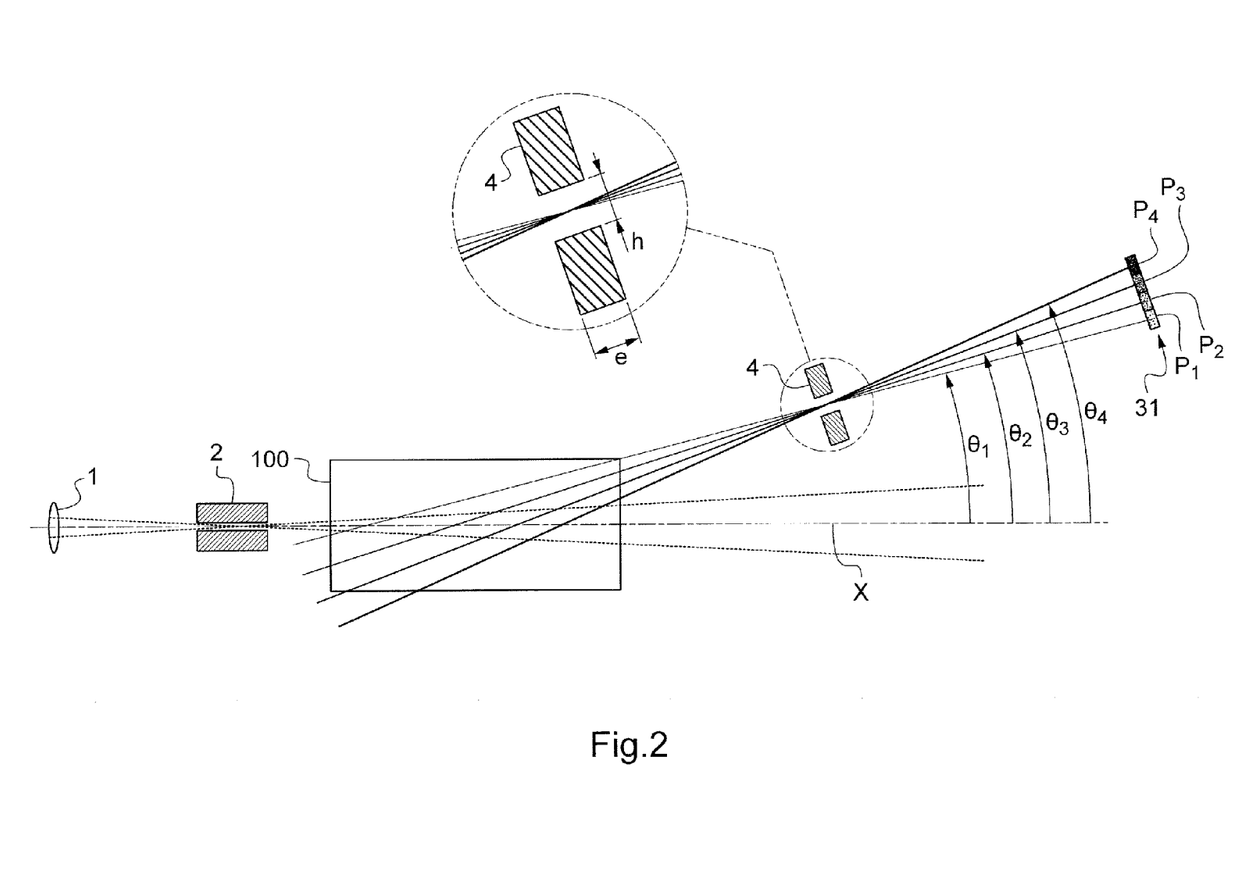
FIG. 2 adopts the diagrammatic view of FIG. 1 while providing a few further details therein.

The diffractometer according to the invention illustrated in FIGS. 1 and 2 makes it possible to observe, in the sample of materials 100, an inspection volume of length L which depends on the opening of the detector collimator 4. If the detector collimator 4 is a narrow collimator, having for example a slot height of 0.4 mm, which corresponds to a diffraction range Δθ of 0.3°, the inspection volume is 63.5 mm³ and the inspection length (along the axis X) is 43 mm. If the detector collimator 4 is an open collimator, having for example a slot height of 2.5 mm, which corresponds to a diffraction range Δθ of 1.6°, the inspection volume is 210 mm³ and the inspection length is 139 mm. The use of such an open detector may be envisioned here thanks to the increase in resolution obtained by the use of a pixelated detector.

Figure 3:
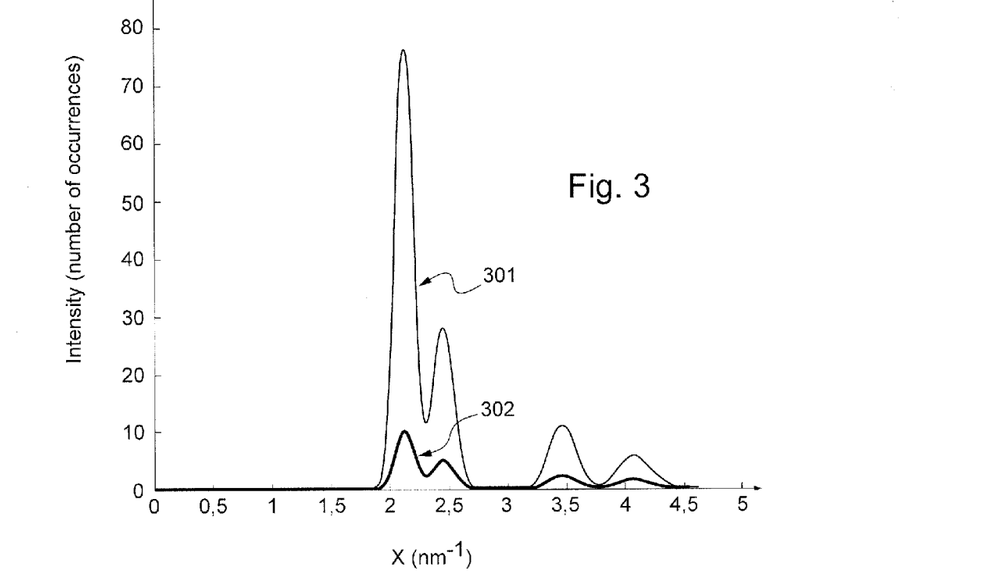
FIG. 3 represents a simulation of two adjusted diffraction spectra which would be obtained for a sample of aluminum by a diffractometer with a pixelated detector according to the invention, by employing a collimator delimiting the detected beam respectively narrowly (this is then termed here a narrow collimator) and widely (this is then termed here an open collimator) along the transverse axis defined earlier.

FIG. 3 represents a simulation of two diffraction spectra. A first spectrum 302 is obtained for a sample of aluminum by the diffractometer of FIGS. 1 and 2, using a narrow collimator (h=0.4 mm). A second spectrum 301 is obtained on that same sample, using an open collimator (h=2.5 mm). In order not to degrade the energy resolution, these spectra are adjusted.

This adjustment preferably consists of a change in variable making it possible to pass, for each pixel Pi of row i constituting the detector, from an energy spectrum to a momentum transfer spectrum (the use of another variable is however possible). It is to be recalled that an energy spectrum is a diagram representing the number of photon interactions found according to the energy E, expressed in keV, released by the interaction; whereas a momentum transfer spectrum is a diagram representing the number of interactions found according to the momentum transfer x, expressed in nm⁻¹, of the interaction. The new variable x is obtained according to the energy E and the diffraction angle θi corresponding to the pixel Pi of row i. For example, this change in variable is governed by the following equation:

$$x = \frac{\sin(\theta_i/2)}{\lambda} = \frac{E\sin(\theta_i/2)}{hc}$$

On account of the change in variable, each spectrum Si(E) corresponding to the pixel Pi of row i is transformed into a spectrum Si(x).

As may be noted on examination of that FIG., the diffraction peaks obtained with the open detection collimator are much greater and more legible than those obtained with the narrow detection collimator. This FIG. illustrates the increase in sensitivity obtained by passing from a narrow collimator to an open collimator, this being without loss in energy resolution. The use of a pixelated detector thus makes opening of the collimation possible in order to improve the sensitivity of the device, since it compensates for the loss in energy resolution of the diffraction peaks which results therefrom.

Figure 6:
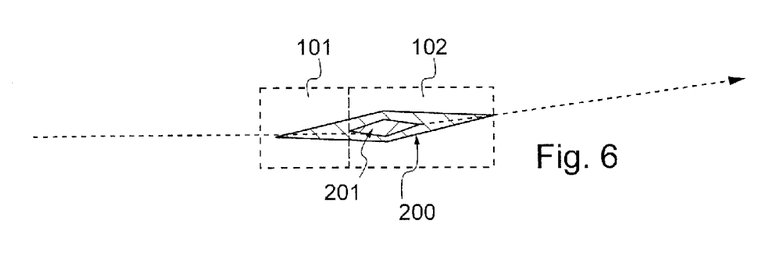
FIG. 6 illustrates a sample of materials 100 constituted by two layers of materials, i.e. a layer of graphite and a layer of salt. The inspection volumes observed, respectively, by a detector with an open collimator, and by a detector with a narrow collimator, are represented in the FIG.

However, the opening of the detection collimator is accompanied by an enlargement of the inspected volume, there is then a high risk of the inspection volume comprising several layers of materials, as illustrated by FIG. 6. This FIG. 6 represents a sample of materials 100 comprising a layer 101 of graphite and a layer 102 of salt. The inspection volume 201 is that observed by the narrow collimator (h=0.4 mm); it only comprises salt. The inspection volume 200 corresponds to that observed by the open collimator (h=2.5 mm), it comprises graphite and salt.

A second important feature is the combination of the spectra by group which makes it possible to get round the problem of confusion of the materials in the spectra obtained.

Prior to this combination, it is advantageous to perform adjustment of the measured energy spectra.

Figure 4A:
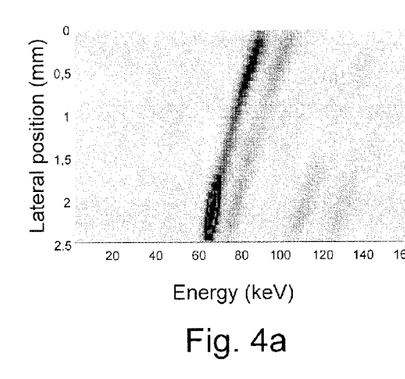
FIG. 4a represents the measured bi-parameter energy spectrum (before adjustment)
Figure 4B:
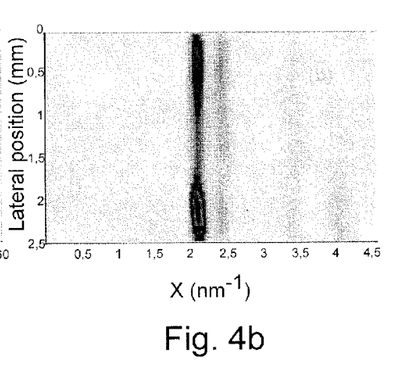
FIG. 4b represents the adjusted bi-parameter spectrum.

FIG. 4a represents energy spectra measured for a mono-material sample entirely constituted by aluminum. FIG. 4b represents the corresponding adjusted spectra. These representations are qualified as bi-parameter representations. The x-axis of FIG. 4a represents, as is conventional in spectrometry, the energy E released by the photon interactions detected. The x-axis of FIG. 4b represents the momentum transfer x. But, in an original way, the energy intensity (that is to say the number of interactions detected for each energy or for each momentum transfer) is not represented on the y-axis but using grayscale. The light areas of the graph show low intensity, contrary to the dark areas which correspond to the diffraction peaks. The y-axis may then be used for another parameter, i.e. the lateral position Yi of the pixel Pi in the detector (position in the transverse direction T). In the same FIG. are thus represented all the measured (FIG. 4a) or adjusted (FIG. 4b) energy spectra obtained for all the pixels of the detector: to each y-coordinate corresponds the spectrum of a pixel. Visually scanning the y-axis amounts to moving in the detector in the direction T. To better understand the adopted representation, it suffices to imagine it in three dimensions. A "cross-section" of the graph at a given lateral position Y corresponds to a "conventional 2D" energy spectrum such as that of FIG. 3.

Figure 7A:
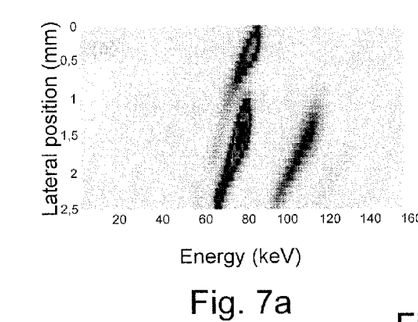
FIG. 7a represents the measured bi-parameter energy spectrum (before adjustment)
Figure 7B:
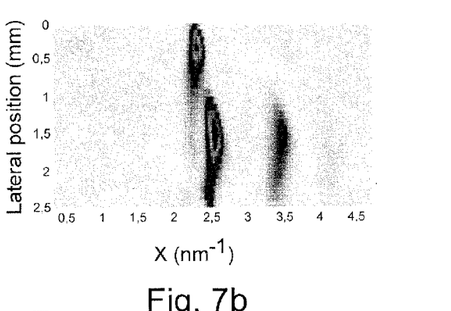
FIG. 7b represents the adjusted bi-parameter spectrum.

FIG. 4 illustrates the measured and adjusted spectra obtained for a monomaterial sample constituted entirely of aluminum. FIG. 7 illustrates the measured and adjusted spectra which were obtained for a multimaterial sample comprising a layer of graphite and a layer of salt; this is the sample 100 illustrated in FIG. 6.

As the combination of the adjusted spectra is carried out, according to the invention, by group, it is thus required to form groups of pixels according to the layers of materials present in the sample.

For this, it is appropriate first of all to determine whether the sample comprises several layers of different materials. To that end, the fulfillment is verified of one or more multimaterial criteria representing the presence of several layers of materials. One of those criteria may be the variation in the adjusted spectra of the position of the first local maximum.

In the bi-parameter spectra of FIGS. 4 and 7, the first local maximum may be identified by the grayscales used: the darkest gray corresponds to the most intense diffraction peak. The first local maximum for a given pixel thus corresponds to the first zone of dark gray surrounded by lighter gray that is encountered on scanning the spectrum along the x-axis at constant y-coordinate.

In the spectra of FIG. 4 which correspond to a monomaterial sample, it is found that the position of the first local maximum does not vary or varies little according to the lateral position: the zones of darker gray are vertically aligned; they correspond to the same momentum transfer for all the pixels.

In the spectra of FIG. 7 which correspond to a graphite/salt multimaterial sample, it is found that the position of the first local maximum varies according to the pixels. It is noted that, for the pixels whose lateral position is comprised between 0 and approximately 1 mm (upper part of the FIG.), the first local maximum is obtained for a momentum transfer x of the order of 2 $nm^{-1}$, whereas for the pixels whose lateral position is greater than 1 mm (lower part of the FIG.), the first local maximum is obtained for a momentum transfer x of the order of 2.3 $nm^{-1}$.

To determine with greater certainty and precision if a change in position of the first local maximum has taken place and, the case arising, at what lateral position Yi (that is to say at what pixel Pi) it took place, a curve is constructed representing the position of the first local maximum in relation to the lateral position.

Figure 5:
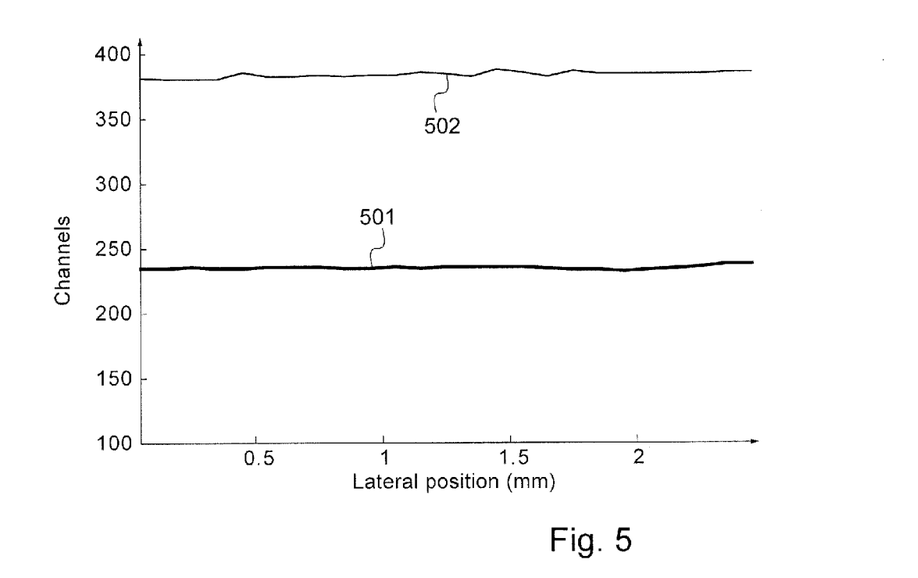
FIG. 5 illustrates a curve representing the position of the first local maximum in relation to the lateral position, and furthermore illustrates a curve representing the position of the second local maximum in relation to the lateral position, of the adjusted spectra of FIG. 4b.

This curve 501 is plotted in FIG. 5 for the monomaterial sample of aluminum; it confirms that the position of the first local maximum varies little according to the pixels: the curve 501 obtained is relatively flat.

Figure 8:
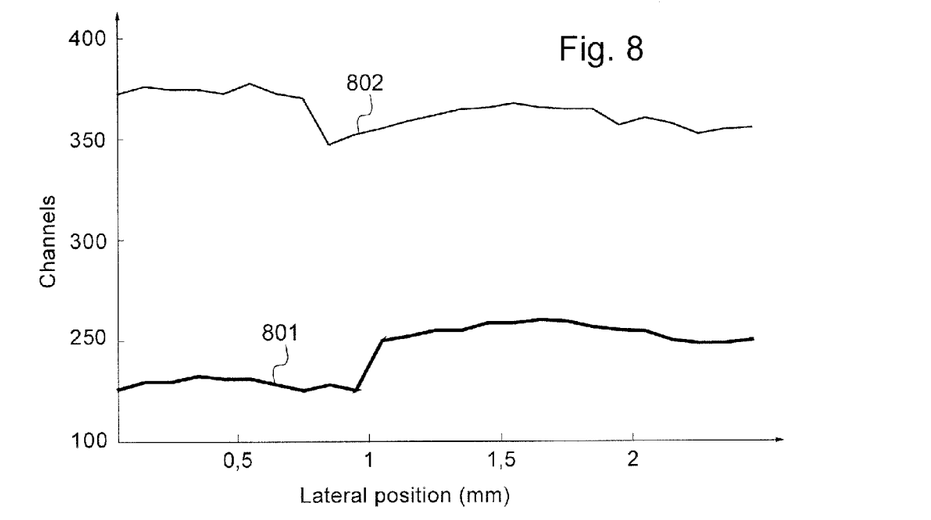
FIG. 8 illustrates a curve representing the position of the first local maximum in relation to the lateral position, and furthermore illustrates a curve representing the position of the second local maximum in relation to the lateral position of the adjusted spectra of FIG. 7b.

The curve for the graphite/salt multimaterial sample can be seen in FIG. 8. The curve 801 obtained shows a steep slope for a lateral position close to 1 mm (of the order of 0.9): the position of the first local maximum varies (drops) there by more than 10% in less than 0.2 mm.

To confirm or possibly refine these results, it is advantageous to verify the fulfillment of a second multimaterial criterion, for example also to study the variation in the position of the second local maximum. The corresponding curves are obtained and represented respectively in FIG. 5 (curve (502) and in FIG. 8 (curve 802) in similar manner to those relative to the first local maximum. In the case of the monomaterial sample (FIG. 5), a curve close to a straight line of zero slope is found. In the case of the graphite/salt multimaterial sample (FIG. 8), a significant jump is again observed for a lateral position Yi equal to 1 mm.

The lateral positions around which a significant variation (jump of the curves 801, 802) from the position of the first and/or the second local maximum is observed, are recorded as constituting the bounds of the groups of pixels. Thus, in the example of the graphite/salt multimaterial sample of FIG. 6, all the pixels for which the lateral position is comprised between 0 and 1 mm are considered as belonging to the first group representing a first material (in this case, graphite); the pixels for which the lateral position is greater than 1 mm are considered as belonging to a second group representing a second material (in this case, salt). In the example of the monomaterial sample of aluminum, the multimaterial criteria not being verified (which means that only one material has been detected), only one group containing all the pixels of the detector is formed.

The adjusted spectra are next summed by group.

Figure 9:
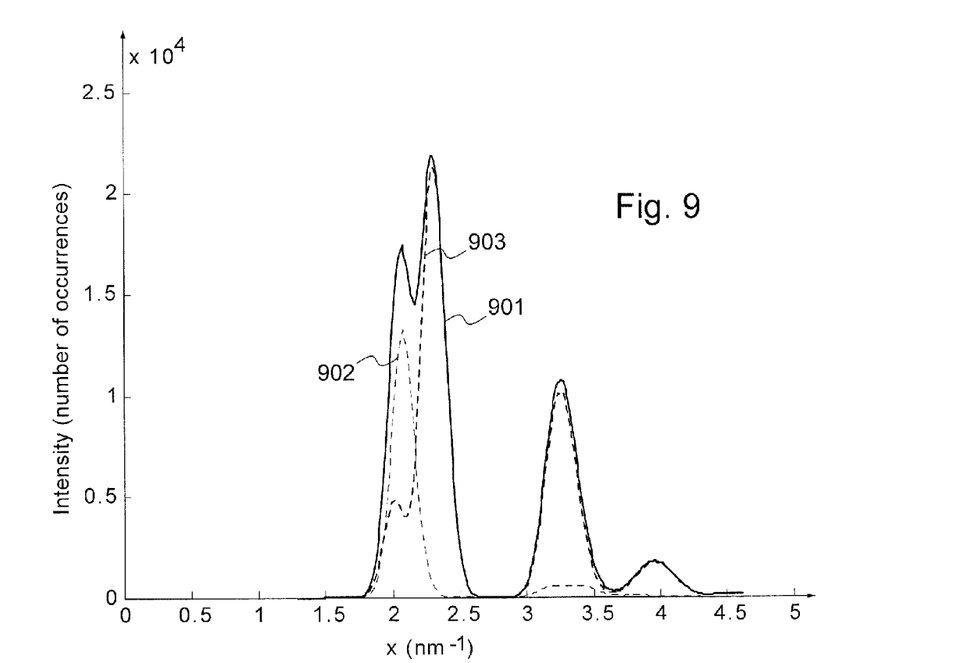
FIG. 9 represents a simulation of adjusted diffraction spectra which would be obtained for the salt/graphite sample of FIG. 6 by a diffractometer with a pixelated detector according to the invention with an open detection collimator. A first spectrum corresponds to the spectrum obtained by combination of all the spectra for the pixels of the detector; a second spectrum corresponds to the spectrum obtained by combination of the spectra of the pixels of the detector having a lateral position comprised between 0 and 1 mm; the third spectrum corresponds to the spectrum obtained by combination of the spectra of the pixels of the detector having a lateral position comprised between 1 mm and 2.5 mm.

FIG. 9 illustrates three combinations of momentum transfer spectra obtained for the graphite/salt multimaterial sample of FIG. 6: the spectrum 901 corresponds to the sum of the adjusted spectra of all the pixels of the detector; the spectrum 902 corresponds to the sum of the adjusted spectra of the pixels of the first group defined above (group corresponding to graphite); the spectrum 903 corresponds to the sum of the adjusted spectra of the pixels of the second group defined earlier (group corresponding to salt).

As can be seen in this FIG. 9, the combination (sum) by group, associated with the pixelation of the detector (which increases the quantity of signals generated), makes it possible, relative to the spectrum 901 obtained for the whole detector:

to separate the peaks into groups, which facilitates the interpretation of the spectra: considering that two peaks which are in reality due to two distinct materials, correspond to the same material, and thus being mistaken in the identification of the material or materials present, is thus avoided, to obtain diffraction peaks that are more intense and narrower, with deeper troughs, which facilitates the identification of the characteristic rays. In other words, the energy resolution is appreciably improved.

It is also to be noted that, as regards the simulations here, no background noise appears on the illustrated spectra. The person skilled in the art will easily understand that in the case of spectra that are really measured, with background noise, the invention even makes it possible to simultaneously increase sensitivity (on account of the reduced detection limit) and energy resolution, and that it furthermore makes it possible to detect the presence of several materials and to reliably define the nature thereof.

The invention may be the object of numerous variants relative to the embodiment illustrated, provided those variants enter the scope delimited by the claims. In particular, the detector may be constituted by pixels distributed in several directions, for example in two directions in the detection plane, and possibly also the direction of the thickness. As the diffraction at a given angle θ takes place in all the directions around the axis X of the incident beam in a cone (of angle θ), the pixelation of the detection plane in two orthogonal directions makes it possible to refine the angular resolution over the whole of the portion of that cone captured by the detector and to increase further still the quantity of signal that is available and processed. In general terms, the row i of the pixel Pi thus varies between 1 and Imax, Imax being the number of pixels, virtual or physical, that the detection plane comprises.

In the example described above, the multimaterial criterion is established by determining the position of the first or second peaks on the adjusted spectra. Other types of criteria may be implemented. For example, the integral $I_i$, that is to say the sum of the channels, may be determined, for each spectrum $S_i$ obtained and it may be concluded that several materials are present when that integral varies significantly, for example by more than 10%, between two adjacent pixels.

Furthermore, the geometry of the diffractometer is not limited to the numerical values provided above. In addition, other methods for combining spectra, relating to spectra adjusted according to a variable (which depends on the energy E or the wavelength λ, as well as the diffraction angle) other than the momentum transfer, may be used.

The invention claimed is:

1. A method of analyzing a sample of materials by diffractometry, the method comprising:
   providing a diffractometer that comprises a source configured to emit an incident beam having a central axis X, and a detector comprising,
   a detector material, which, on a near side to the sample of materials, presents a detection plane,
   spectrometry measurement means, configured to measure an energy released by each photon interaction with the detector material and to establish at least one measured spectrum;
      a detection collimator, associated with the detector, the detector and the detection collimator being arranged so as to have a detection axis D forming a diffraction angle θ with the central axis X of the incident beam;
   irradiating the sample with the incident beam,
   wherein the detector comprises a pixelated detector comprising means for locating an interaction of a photon with the detector material (30), so as to define a partition of the detector in physical or virtual pixels (Pi), and associating one of the physical or virtual pixels with each photon interaction;
   establishing an energy spectrum for each physical or virtual pixel of the detector;
   adjusting each measured energy spectrum (E), by expressing the energy spectrum according to a variable that accounts for an energy of scattered radiation and the diffraction angle $θ_i$, to obtain an adjusted spectra, for each measured energy spectrum;
   verifying fulfillment of at least one multimaterial criterion representing the presence of several layers of materials;
   forming groups of pixels using results of the verifying step, each group corresponding to a layer of material, where different groups correspond to different layers of material; and
   combining spectra by group for each group, where the adjusted spectrum obtained for the pixels (Pi) of the group are combined.

2. A method according to claim 1, wherein the adjusted spectra comprises spectra Si(x) in terms of momentum transfer, where a change in variable is carried out using the following formula:

$$x = \frac{\sin(\theta_i/2)}{\lambda} = \frac{E\sin(\theta_i/2)}{hc},$$

where $θ_i$ designates the diffraction angle corresponding to the pixel Pi, where the diffraction angle is between the central axis X of the incident beam and an axis Di passing by the center of the pixel Pi and the center of the detection collimator, and λ is a wavelength corresponding to the energy E; and,
wherein combining spectra by group, for each group, comprises summing the adjusted spectra Si(x) of the pixels of the group.

3. A method according to one of the preceding claims, wherein the at least one multimaterial criterion comprises one of:
   a variation greater than 10% of a position in the adjusted spectra of a first local maximum, between two adjacent pixels in a transverse direction (T), orthogonal to the detection axis (D);
   a variation greater than 10% of a position in the adjusted spectra of a second local maximum, between two adjacent pixels in the transverse direction; or
   a variation greater than 10% of a sum of the channels of the adjusted spectrum of each pixel, between two adjacent pixels in the transverse direction.

4. A method according to claim 3 further comprising constructing a curve representing, along a y-axis, the position in the adjusted spectra of the first or second local maximum, based, along an x-axis, on a lateral position (Yi) of the pixel (Pi) or on its diffraction angle θi.

5. A method according to claim 1, wherein the detector comprises a detector having a pixelated detection plane.

6. A method according to claim 1, wherein the detector comprises a semiconductor detector material.

7. A method according to claim 1, wherein the source comprises a polychromatic source, and produces radiation having a maximum energy is about 10 keV to about 200 keV.

8. A method according to claim 1, wherein the diffraction angle θ is about 2° to about 10°.

9. A method according to claim 1, wherein the detection collimator comprises an open slot collimator having slot with a height greater than 1 mm.

10. A diffractometer configured to analyze a sample of materials, the diffractometer comprising:
   a source configured to emit an incident beam having a central axis X,
   a detector comprising,
   a detector material, which, on a near side to the sample of materials, presents a detection plane,
   spectrometry measurement means, configured to measure an energy released by each photon interaction with the detector material and to establish at least one measured energy spectrum;
      a detection collimator, associated with the detector, the detector and the detection collimator being arranged so as to have a detection axis D forming a diffraction angle θ with the central axis X of the incident beam, wherein
   the detector is pixelated and comprises means for locating an interaction of a photon with the detector material, so as to define a partition of the detector in physical or virtual pixels, and associating one of the physical or virtual pixels with each photon interaction,
   the spectrometry measuring means are configured to establish an energy spectrum Si(E) for each pixel (Pi) of the detector, and
   the diffractometer further comprises
   adjusting means configured to establish, for each at least one measured energy spectrum, an adjusted spectrum expressed according to a variable that accounts for an energy of scattered radiation and the diffraction angle $\theta_i$, means for verifying fulfillment of at least one multimaterial criterion representing a presence of several layers of materials, means for forming groups of pixels, each group corresponding to a layer of material, where different groups correspond to different layers of material, and means for combining spectra by group, adapted, for each group, to combine the adjusted spectra obtained for the pixels of the group.

11. A diffractometer according to claim 10, wherein the adjusting means are configured to establish, for each pixel (Pi), a momentum transfer spectrum $S_i(x)$, from the measured spectrum Si(E) by a change in variable using the formula $$x = \frac{\sin(\theta_i/2)}{\lambda} = \frac{E\sin(\theta_i/2)}{hc}$$

where $\theta_i$ designates the diffraction angle corresponding to the pixel (Pi) and $\lambda$ is a wavelength corresponding to the energy E, the means for combining spectra by group are configured to calculate the sum of the adjusted spectra Si(x) of pixels of a same group.

12. A diffractometer according to claim 10, wherein,
the means for verifying fulfillment of at least one multimaterial criterion are configured to establish a curve representing a position of a first local maximum in the adjusted spectrum of a pixel Pi, along a y-axis, according to an angle of observation $\theta i$ of the pixel Pi or a lateral position Yi thereof, along an x-axis, the lateral position Yi being defined as a coordinate of the pixel Pi in a transverse direction (T), orthogonal to the detection axis D and contained in a detection plane (X,D), the means for forming groups of pixels are configured to group together within a same group two adjacent pixels $P_i$ and $P_{i+1}$ in the transverse direction if and only if the difference between the position of the first local maximum in the spectrum of the pixel $P_i$ and the position of the first local maximum in the spectrum of the pixel $P_{i+1}$ do not vary by more than 10%.

13. A diffractometer according to claim 10, wherein the detector material of the detector comprises a semiconductor material.

14. A diffractometer according to claim 10, wherein the diffraction angle $\theta$ is between about 2° to about 10°.

15. A diffractometer according to claim 10, wherein the detection collimator comprising an open slot collimator having slot with a height (h) greater than 1 mm.

* * * * *

UNITED STATES PATENT AND TRADEMARK OFFICE
CERTIFICATE OF CORRECTION

PATENT NO.        : 9,599,580 B2                              Page 1 of 1
APPLICATION NO.   : 14/428721
DATED             : March 21, 2017
INVENTOR(S)       : Bahaa Ghammraoui et al.

It is certified that error appears in the above-identified patent and that said Letters Patent is hereby corrected as shown below:

On the Title Page

Item (73) Assignees, please delete "; MOZIDO, INC., Austin, TX (US)".

Signed and Sealed this
First Day of June, 2021

Drew Hirshfeld
*Performing the Functions and Duties of the*
*Under Secretary of Commerce for Intellectual Property and*
*Director of the United States Patent and Trademark Office*